United States Patent [19]

Watson et al.

[11] 4,033,994

[45] July 5, 1977

[54] SUBSTITUTED p-MENTHANES

[75] Inventors: Hugh R. Watson, Wargrave; David G. Rowsell, Staines; John H. D. Browning, Wokingham, all of England

[73] Assignee: Wilkinson Sword Limited, England

[22] Filed: July 8, 1974

[21] Appl. No.: 486,652

Related U.S. Application Data

[63] Continuation-in-part of Ser. No. 221,753, Jan. 28, 1972, abandoned.

[52] U.S. Cl. .......................... 260/468 R; 131/17 R; 260/340.9; 260/484 A; 260/489; 424/305; 424/307; 426/538

[51] Int. Cl.² .......................................... C07C 69/74
[58] Field of Search ............ 200/408 R, 489, 484 A

[56] References Cited

FOREIGN PATENTS OR APPLICATIONS 2,202,535  8/1972  Germany ........................ 260/468

Primary Examiner—Robert Gerstl
Attorney, Agent, or Firm—Leydig, Voit, Osann, Mayer & Holt, Ltd.

[57] ABSTRACT

Compounds are disclosed having a physiological cooling action on the skin. The compositions contain, as the effective ingredient, certain esters of p-menthane 3-carboxylic acid.

6 Claims, No Drawings

SUBSTITUTED p-MENTHANES

RELATED APPLICATIONS

This application is a continuation-in-part of application Ser. No. 221,753 filed Jan. 28, 1972 now abandoned.

FIELD OF THE INVENTION

This invention relates to compounds having a physiological cooling effect on the skin and on the mucous membranes of the body, particularly those of the mouth, nose, throat and gastrointestinal tract.

BACKGROUND OF THE INVENTION AND PRIOR ART

Menthol is well known for its physiological cooling effect on the skin and mucous membranes of the mouth and has been extensively used as a flavouring agent (menthol being a major constituent of oil of peppermint) in foodstuffs, beverages, dentifrices, mouthwashes, etc. and as a component in a wide range of toiletries, liniments and lotions for topical application. Menthol is also a well known tobacco additive for producing a "cool" sensation in the mouth when smoking.

It is well established that the cooling effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use, in some compositions, is circumscribed by its strong minty odour and its relative volatility.

A few other compounds have been reported in the technical literature as having an odour or flavour similar to menthol and from time to time have been proposed as flavourants or odourants in a variety of topical and ingestible compositions. For example, Japanese Patent Publication No. 39-19627 reports that 3-hydroxymethyl p-menthane (menthyl carbinol) has a flavour closely resembling that of l-menthol and suggests its use as a flavourant in confectionery, chewing gum and tobacco. In Swiss patent No. 484,032 certain saccharide esters of menthol are proposed as additives to tobacco. In French Pat. No. 1,572,332 N,N-Dimethyl 2-ethylbutanamide is reported as having a minty odour and refreshing effect, and the minty odour of N,N-diethyl 2,2-dimethylpropanamide is referred to. A similar effect is reported for N,N-diethyl 2-ethylbutanamide in Berichte 39, 1223, (1906). A minty odour has also been reported for 2,4,6-trimethylheptan-4-ol and 2,4,6-trimethyl hept-2-on-4-ol in Parfums-Cosmetiques-Savons, May 1956, pp. 17–20. The cooling effect of menthol and other related terpene alcohols and their derivatives has also been studied and reported in Koryo, 95, (1970), pp. 39–43. 2,3-p-menthane diol has also been reported as having a sharp cooling taste (Beilstein, Handbuch der Organischen Chemie, 4th Ed. (1923) Vol. 6, p. 744).

Despite this knowledge of other compounds having an odour and flavour similar to that of menthol, menthol is still extensively used in topical, ingestible and other compositions notwithstanding the disadvantages mentioned above, namely its very strong odour and its relative volatility.

OBJECTS OF THE INVENTION

It is an object of the present invention to provide other compounds having a pronounced physiological cooling effect, in many cases far more persistent than that obtained with menthol, without the attendant disadvantages of a strong odour.

It is a further object to provide compounds having a pronounced physiological cooling effect and being of relatively low volatility.

SUMMARY OF INVENTION

According to the present invention there is provided a novel group of 3-substituted-p-menthanes which have a pronounced physiological cooling activity, which have little or no odour, which are of relatively low volatility and which are substantially non-toxic. These compounds are 3-substituted-p-menthanes of the formula:

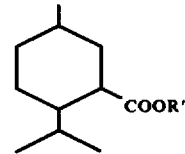

where R' is an aliphatic radical of up to 10 cabon atoms selected from: hydroxyaliphatic radicals containing from 2 to 10 carbon atoms and having a hydroxyl substituent in a 2, 3 or 4-position and a hydrogen atom in the 1-position; a ketal derivative of such a hydroxyaliphatic radical with a lower ketone (e.g. acetone); a lower acyl (e.g. acetyl) derivative of such a hydroxyaliphatic radical; a lower alkylene oxide (e.g. ethylene oxide, propylene oxide) adduct of such a hydroxyaliphatic radical; hydroxyaryl radicals having a hydroxyl substituent in a 2- or 3-position relative to the ester grouping; carboxyaliphatic radicals having a carboxyl group in a 1-, 2- or 3-position; an alkali metal (e.g. Na or K), alkaline earth metal (e.g. Ca or Mg), ammonium or substituted ammonium (e.g. ethanolamine or trimethylamine) salt of such a carboxyaliphatic radical; and lower alkyl esters of such a carboxyaliphatic radical.

DEFINITIONS

By 'hydroxyaliphatic' we mean a hydrocarbyl group free of aromatic unsaturation, having a hydroxyl group in the specified position relative to the ester (—COO—) grouping, but being otherwise essentially free of functional groups. Hydroxyaliphatic therefore embraces hydroxyalkyl, hydroxycycloalkyl, hydroxyalkenyl, hydroxyalkynyl, hydroxyalkylcycloalkyl and hydroxycycloalkylalkyl and similar combinations. Particular hydroxyaliphatic groups include 2-hydroxyethyl, 2-hydroxypropyl, 2,3-dihydroxypropyl, sorbityl, 2-hydroxycyclohexyl, 2-hydroxycyclohexylmethyl, 2-hydroxy-4-methylcycloyhexyl, 2-hydroxy - 1,2-dimethylethyl and 2-hydroxy-1-methylethyl etc.

By 'carboxyaliphatic' we mean a hydrocarbyl group free of aromatic unsaturation, having a carboxyl group in the specified position relative to the ester (—COO—) grouping, but being otherwise essentially free of functional groups. Carboxyaliphatic therefore includes carboxyalkyl, carboxycycloalkyl, carboxyalkenyl, carboxyalkynyl, carboxyalkylcycloalkyl, carboxycycloalkylalkyl and similar combinations. Typical carboxyaliphatic groups include 1-carboxyethyl, 2-carboxyethyl, 2-carboxypropyl, 3-carboxypropyl, 3-carboxypropenyl, 3-carboxypropynyl, 2-carboxycyclohexyl, 2-carboxycyclohexylmethyl, 4-methyl-2-carboxycyclohexyl etc.

By 'hydroxyaryl' we mean a hydrocarbyl group containing aromatic unsaturation, having a hydroxyl group in the specified position relative to the ester (—COO—) grouping, but being otherwise essentially free of functional groups. Hydroxyaryl therefore includes aralkyl, alkaryl and like combinations. As indicated, the hydroxyaryl group will contain a hydroxyl group in a 2- or 3-position relative to the ester grouping; this may be a nuclear hydroxyl group as in orthohydroxybenzyl, orthohydroxyphenyl or orthohydroxynaphthyl or in a side chain as in 1-phenyl-2-hydroxyethyl or O-(hydroxymethyl)phenyl.

By 'substituted ammonium' in all instances we mean salts with organic amines, and in particular alkylamines e.g. mono, di- and trialkylamines and alkanolamines e.g. ethanolamine.

By 'lower' in all instances we mean containing from 1-4 carbon atoms.

By 'essentially free' of functional groups in all instances we mean free of substituent groups such as amino, alkylamino, alkoxy, acyloxy in positions which interfere with the physiological cooling activity.

DETAILED DESCRIPTION

The 3-substituted-p-menthanes used according to this invention may be readily prepared by conventional methods. Thus, p-menthane-3-carboxylic acid may readily be prepared by carbonation of a Grignard reagent derived from menthol. The carboxylic acid may then readily be converted into its acid chloride, for example, by reaction with thionyl chloride, and the acid chloride converted into the desired ester derivative by reaction with an appropriate alcohol. Other methods for the preparation of the esters of this invention will be apparent to those skilled in the art.

The compounds provided in accordance with this invention exhibit both geometric and optical isomerism and, depending on the starting materials and the methods used in their preparation the compounds may be isomercially pure, i.e. consisting of one geometric or optical isomer, or they may be isomeric mixtures, both in the geometric and optical sense.

As is well known, the basic p-menthane structure is a chair-shaped molecule which can exist in cis or trans forms. Substitution of the carboxyl group into the 3-position gives rise to four configurational or geometric isomers depending upon whether the substitution is axially or equatorially into the cis or trans isomer, the four isomers being related as menthol is to neomenthol, isomenthol, and neoisomenthol. In general it is found that in the compounds used in this invention the equatorially substituted derivatives have a greater cooling effect than the axial compounds and are to be preferred.

Substitution of the carboxyl group in the 3-position of the p-menthane structure also gives rise to optical isomerism, each of the above-mentioned four geometric isomers existing in d, l and dl forms. The physiological cooling effect is found, in most cases, to be greater in the l-form than in d-form, and in some cases substantially greater. The derivatives of the l-acid are therefore preferred.

The cooling sensation created by the compounds used in this invention on the skin and mucous membranes, for example, in the mouth, varies both in intensity and longevity from compound to compound.

Preferred compounds provided in accordance with this invention are those of the formula hereinbefore given where R' is a $C_2$–$C_{10}$ hydroxyalkyl group having a hydroxyl substituent in the 2- or 3-position relative to the ester grouping; an aryl group having a hydroxyl substituent in an ortho position and a total of up to 10 carbon atoms; a carboxyalkyl group of up to 10 carbon atoms having a carboxy group in a 1, 2- or 3-position relative to the ester grouping; or a lower alkyl ester of such a carboxyalkyl group. Most preferred are the 2-hydroxy (lower) alkyl esters, and particularly the 2-hydroxyethyl ester; and the adducts of these 2-hydroxy (lower) alkyl esters with from 1-3 molecules of ethylene oxide.

For the purposes of the present disclosure the following test procedure has been devised as a means to identify compounds having a physiological cooling activity in accordance with the present invention and herein referred to as cold receptor stimulants. This test is intended purely as a means for identifying compounds having a physiological cooling activity and useful in the present invention and for giving an indication of the different relative activities of the compounds, as between themselves and as compared with menthol, when applied in a particular manner to a particular part of the body. The results are not necessarily indicative of the activity of these compounds in other formulations and other parts of the body where other factors come into play. For example, a controlling factor in the onset of cooling effect, its intensity and longevity will be the rate of penetration of the compounds through the epidermis and this will vary in different locations on the human body. The formulation of actual products according to this invention will therefore be done largely on an empirical basis although the test results and other figures given herein will be useful as a guide, particularly in the formulation of products for oral administration, since the test procedure to be described involves oral application of the compound. A similar test may, of course, be devised for the purposes of measuring the relative activities of the compounds on another area of the body, for example, the face or forearm, and this will be a useful guide in the choice of compounds to be used in preparations for external topical usage.

It will also be noted that the described test procedure is done on a statistical basis. This is necessary since sensitivity to these compounds will vary not only from compound to compound and from one part of the body to another, but also from one individual to another. Tests of this nature are commonly used in the testing of the organoleptic properties, e.g. taste, smell etc. of organic and inorganic compounds, see Kirk-Othmer: Encyclopedia of Chemical Technology, 2nd.Ed. (1967) Vol. 14 pages 336 –344

TEST PROCEDURE

The following test procedure is aimed at determining the minimum quantity of the test compound required to produce a noticeable cooling effect on a person of average sensitivity, this minimum quantity being termed the threshold for that particular compound.

The tests are carried out on a selected panel of six people of median sensitivity to 1-menthol.

PANEL SELECTION

To select a test panel of average sensitivity the following procedure is used. Known quantities of 1-menthol in solution in petroleum ether (bp. 40–60) are placed on 5 mm. squares of filter paper, whereafter the solvent is allowed to evaporate. A panel of observers is enrolled and asked to place one impregnated square at time on the tongue and to report on the presence or absence of a cooling effect. The quantity of 1-menthol on each impregnated square is gradually reduced from a value substantially above 0.25 $\mu$g. per square to substantially below 0.25 $\mu$g, the precise range being immaterial. Conveniently, one starts with squares containing 2.0 $\mu$g. 1-menthol, the amount on each successive square being half that of the preceding square, i.e. the second test square will contain 1.0 $\mu$g, the third 0.5 $\mu$g. and so on. Each quantity is tested on the tongue at least 10 times. In this way, the thresholds to cold receptor stimulus by 1-menthol are determined for each individual of the panel, the threshold for each individual being that amount of 1-menthol for which, in a series of not less than 10 test applications, a cooling effect is reported 50% of the time. Six panel members are now selected whose threshold to 1-menthol is in the range 0.1 to 10 $\mu$g. and whose average threshold is approximately 0.25 $\mu$g., this select panel being regarded as the test panel of average sensitivity.

COMPOUND TESTING

To test the activity of compounds according to this invention, the above procedure is repeated using only the six selected panel members of average sensitivity to 1-menthol. The individual thresholds for each test compound on each of the six selected panel members are determined and averaged. Those compounds whose average threshold on the select test panel is 100 $\mu$g. or less are regarded as having cooling activity in accordance with this invention.

TEST RESULTS

The following table sets out the relative cooling activities of compounds of the formula defined above when tested according to the foregoing procedure.

TABLE

| Compound | Threshold ($\mu$g) |
| --- | --- |
| p-menthane-3-carboxylic acid esters where ester moiety equals: | |
| —CH$_2$CH$_2$OH | 1.5 |
| —CH$_2$CH(OH)CH$_2$OH | 1.2 |
| —CH$_2$CH(OH)CH$_3$ \ Isomeric Mixture | 1.4 |
| —CH(CH$_2$OH)CH$_3$ / | |
| —CH$_2$(CHOH)$_4$CH$_2$OH | 50 |
| —CH$_2$CH$_2$OCOCH$_3$ | 33 |
| —CH$_2$CH$_2$CH$_2$OH | 7 |
| —CH(CH$_3$)CH(CH$_3$)OH | 3 |
| —CH$_2$CH(OH)n-C$_4$H$_9$ \ Isomeric Mixture | 8 |
| —CH(CH$_2$OH)n-C$_4$H$_9$ / | |
| —CH$_2$CH(OH)n-C$_6$H$_{17}$ | 90 |
| —CH$_2$(CHOH)$_2$CH$_2$OH | 50 |
| —CH$_2$CH$_2$(OCH$_2$CH$_2$)$_2$OH | 5 |
| —CH$_2$CH$_2$OCH$_2$CH$_2$OH | 1.0 |
| —CH$_2$CH$_2$(OCH$_2$CH$_2$)$_{2.75}$OH | 15 |
| (phenyl with HO) | 5 |

TABLE-continued

| Compound | Threshold ($\mu$g) |
| --- | --- |
| (cyclohexyl with HO) | 4 |
| (phenyl with OH and CH$_3$) | 15 |
| —CH$_2$—CH—CH$_2$ with O-C(CH$_3$)$_2$-O ring | 11 |
| —CH(CH$_3$) COOH | 8 |
| —CH$_2$CH$_2$COOH | 10 |
| —C(CH$_3$)$_2$COOH | 20 |
| —CH(CH$_3$)COOC$_2$H$_5$ | 50 |
| —CH$_2$COOH | 15 |
| —CH$_2$CH$_2$CH$_2$CH$_2$OH | 12 |
| —CH$_2$C≡CCH$_2$OH | 6 |

UTILITY

The compounds of this invention find utility in a wide variety of consumer products for consumption by or application to the human body. Broadly speaking, these products can be divided into comestible and topical compositions, both terms being taken in their broadest possible sense. Thus comestible is to be taken as including not only foodstuffs and beverages taken into the mouth and swallowed, but also other orally ingested compositions taken for reasons other than their nutritional value, e.g. indigestion tablets, antacid preparations, laxatives etc. Comestible products are also to be taken to include edible compositions taken by mouth, but not necessarily swallowed, e.g. chewing gum. Topical compositions are to be taken as including not only compositions such as perfumes, powders and other toiletries, lotions, liniments, oils and ointment applied to the external surfaces of the human body, whether for medical or other reasons, but also compositions applied to, or which, in normal usage, come in contact with, internal mucous membranes of the body, such as those of the nose, mouth, or throat, whether by direct or indirect application or inhalation, and thus include nasal and throat sprays, dentifrice, mouthwash and gargle compositions. Topical compositions are also to be taken to include toilet articles such as cleansing tissues and toothpicks.

A further class of compositions into which the compounds of this invention can usefully be incorporated are tobacco and associated articles e.g. pipe and cigarette filters, especially filter tips for cigarettes.

Compounds according to this invention are illustrated by the following Examples. All temperatures are given in degrees Centigrade.

EXAMPLE 1

Preparation of 2-Hydroxyethyl p-Menthane-3-Carboxylate

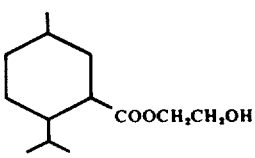

A mixture of p-menth-3-oyl chloride (4.0 g., 0.02 moles) and ethylene gylcol (12 g.) was stirred at room temperature for 5 hours. At the end of this time the reaction mixture was poured into water (500 ml.), extracted twice with ether and dried ($MgSO_4$). Removal of the solvent left one major component. Distillation of the oil yielded 2-hydroxyethyl p-menthane-3-carboxylate, b.p. 92°–4°/0.1 mm. as a colourless liquid.

EXAMPLE 2

Preparation of 2-Acetoxyethyl p-Menthane-3-Carboxylate 2-hydroxyethyl p-menthane-3-carboxylate (3.0 g.) in ether (5 ml.) was treated dropwise with a solution of acetyl chloride (2 ml.) in ether (15 ml.). The mixture was heated under reflux for 5 hours, cooled and washed with saturated aqueous sodium bicarbonate and water. The ether layer was dried ($MgSO_4$), and concentrated in vacuo to give 2-acetoxyethyl p-menthane-3-carboxylates, (2.8 g., 76%) b.p. 97°–9°/.05 mm.

EXAMPLE 3

Preparation of Glucitol p-Menthane-3-Carboxylate

A solution of sorbitol (0.78 g.) in dry pyridine (20 ml.) was treated dropwise with a solution of p-menth-3-oyl chloride (0.86 g.) in pyridine (10 ml.). After 18 hour at room temperature, the pyridine was evaporated under reduced pressure, final traces being removed by co-distillation with toluene. The residue was dissolved in water and extracted with ether (3 × 50 ml.). Concentration of the aqueous layer yielded an amorphous mixture of 1- and 6-p-menthane-3-carboxylate of glucitol (0.6 g., 40%).

EXAMPLE 4

Preparation of p-Menthane-3-Carboxylic Acid 2-Hydroxy-1-Methyl-propyl Ester

A mixture of p-menth-3-oyl chloride (2.4 g.) and 2, 3-butanediol (20 ml.) was stirred at room temperature for 17 hours, then poured into water (700 ml.), extracted twice with ether, and the extracts dried ($MgSO_4$). Removal of the solvent left a colourless oil (3.3 g.) which was distilled to yield p-menthane-3-carboxylic acid 2-hydroxy-1-methyl-propyl ester, (Found C, 71.1; H, 10.9; $C_{15}H_{28}O_3$ requires C, 70.3; H, 10.9%) as a colourless liquid, b.p. 94°–95°/0.1 mm.

EXAMPLE 5

Preparation of 4-(p-Menth-3-Oyloxymethyl)2,2-Dimethyl-1, 3-Dioxolan

A mixture of p-menth-3-oyl chloride (3.0 g.) and 1, 2-isopropylidene glycerol (10 ml.) was stirred at room temperature for 2 hours, then poured into saturated $Na_2CO_3$ solution (300 ml.), extracted twice with light petrol (b.p. 40°–60°) and the extracts dried ($CaCl_2$). Removal of the solvent left an oil (5 g.) which was distilled to yield 4-(p-menth-3-oyloxymethyl)-2,2-dimethyl-1,3-dioxolan as a colourless liquid b.p. 113°/0.1 mm.

EXAMPLE 6

Preparation of 1-(p-Menth-3-oyl)Glycerol 4-(p-Menth-3-oyloxy)-2,2-dimethyl-1,3-dioxolan (3 g.) was stirred for 5 minutes at room temperature with 90% $CF_3COOH$ (15 ml.), and the $CF_3COOH$ removed in vacuo. The residual oil was stirred for 4 hours at room temperature with a solution of $K_2CO_3$ (7%) in water:methanol (2:5) (50 ml.). The methanol was removed on a rotary evaporator, water (30 ml.) added and the mixture extracted four times with ether. The combined extracts were dried ($MgSO_4$). Removal of the ether left an oil which was distilled to yield 1-(p-menth-3-oyl)glycerol as a colourless liquid b.p. 135°/0.1 mm.

EXAMPLE 7

Preparation of 1,2-Bis(p-Menth-3-oyl)Glycerol

A mixture of p-menth-3-oyl chloride (2 g.) and glycerol (20 ml.) was heated at 100° for 4 hours. The mixture was then poured into water (600 ml.) and extracted 3 times with ether. The extracts were dried ($MgSO_4$) and the solvent removed under reduced pressure to leave 1,2-bis-(p-menth-3-oyl)glycerol as a colourless oil (1.2 g.).

EXAMPLE 8

Preparation of Ortho-Hydroxyphenyl p-Menthane-3-Carboxylate p-Menth-3-oyl chloride (2.0 g.) and pyrocatechol (1.1 g.) were heated under refluxing conditions in toluene (75 ml.) for 4 hours. An oily liquid was recovered which was identified as ortho-hydroxyphenyl p-menthane-3-carboxylate.

EXAMPLE 9

Preparation of 2-(p-Menth-3-Oyloxy)Propionic Acid p-Menth-3-oyl chloride (2.0 g.) was stirred with lactic acid (20 ml.) at room temperature for 20 hours. The reaction product was then poured into water (600 ml.) and extracted twice with ether. The extracts were dried ($CaCl_2$) and the solvent removed under reduced pressure to leave 2-(p-menth-3-oyloxy)propionic acid as an oily liquid.

EXAMPLE 10

Preparation of 2-Hydroxypropyl p-Menthane-3-Carboxylate

Repeating the procedure of Example 1 using 1,2 -propane diol (12 g.) in place of ethylene glycol yielded an oily liquid — b.p. 89°/0.1 mm, containing an isomeric mixture of 2-hydroxypropyl p-menthane-3-carboxylate and 2-(p-menth -3-oyloxy)propanol.

EXAMPLE 11

Preparation of 2-(2'-Hydroxyethoxy)Ethyl p-Menthane-3-Carboxylate p-Menthane-3-carbonyl chloride (6.0 g.) in acetone (50 ml.) was added dropwise to a stirred mixture of triethylamine (3.0 g.), diethylene glycol (20 g.) and acetone (100 ml.) at room temperature. After stirring overnight the acetone was removed on a rotary evaporator, water and excess 2N H₂SO₄ were added and the mixture extracted three times with ether. The combined extracts were washed with dilute caustic soda solution and then dried (MgSO₄). Removal of the solvent left an oil which was distilled under vacuum to yield 2-(2'-hydroxyethoxy) ethyl p-menthane-3-carboxylate as a colourless liquid b.p. 130°–2°/0.03 mm. (6.5g., 80%).

EXAMPLE 12

Preparation of 2'-Hydroxyethyl p-Menthane-3-Carboxylate (Ethylene Oxide)₂ Adduct The procedure of Example 11 was repeated using triethylene glycol in place of the diethylene glycol. The product was identified as the (ethylene oxide)₂ adduct of 2'-hydroxyethyl p-menthane-3-carboxylate, viz:

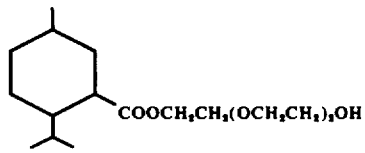
COOCH₂CH₂(OCH₂CH₂)₂OH b.p. 166°–70°/0.01 mm.

EXAMPLE 13

Preparation of 2'-Hydroxyethyl p-Menthane-3-Carboxylate (Ethylene Oxide)₂.₇₅ Adduct The procedure of Example 11 was repeated using polyethylene glycol 200 in place of diethylene glycol. The product was identified as the (ethylene oxide)₂.₇₅ adduct of 2'-hydroxyethyl p-menthane-3-carboxylate, viz:

COOCH₂CH₂(OCH₂CH₂)₂.₇₅OH b.p. 170°–220°/0.02 mm.

We claim:
1. Compounds of the formula:

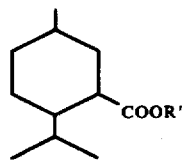
COOR' where R' is an aliphatic radical of up to 10 carbon atoms selected from: mono- and poly-hydroxyalkyl and cycloalkyl radicals containing from 2 to 10 carbon atoms and having a hydroxyl group in one or more of the 2-, or 3-position and a hydrogen atom in the 1-position; (2,2-dimethyl-1,3-dioxolan-4-yl) methyl; an acylated derivative of a hydroxyalkyl radical of 2–9 carbon atoms with a lower alkanoic acid; an aryl hydrocarbon radical of up to 10 carbon atoms and containing a hydroxyl substituent in a 2- or 3-position relative to the ester grouping; carboxyalkyl radicals containing a carboxyl group in the 1-, 2- or 3-position; and alkali metal, alkaline earth metal, ammonium or substituted ammonium salt of such a carboxyalkyl radical; and lower alkyl esters of such carboxyalkyl radicals.

2. Compounds of the formula:

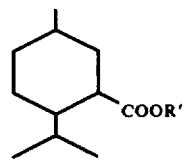
COOR' wherein R' is a C₂–C₁₀ hydroxyalkyl group having a hydroxyl group in the 2- or 3-position; an aryl hydrocarbon group having a hydroxy group in an ortho position and a total of up to 10 carbon atoms; a carboxyalkyl group of up to 10 carbon atoms having a carboxyl group in the 1-, 2- or 3-position; or a lower alkyl ester of such a carboxyalkyl group.

3. Compounds according to claim 1, wherein R', wherein R', in the general formula, represents a 2-hydroxy lower alkyl group.

4. 2'-Hydroxyethyl p-menthane-3-carboxylate.

5. Adducts of 2'-hydroxyethyl p-menthane-3-carboxylate with from 1 - 3 molecules of ethylene oxide.

6. Compounds of the formula:

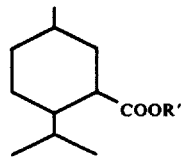
COOR' wherein R' is a radical containing up to 10 carbon atoms, said radical being an adduct of a hydroxyalkyl radical of at least 2 carbon atoms and having a hydroxyl group in the 2, or 3-position and a hydrogen atom in the 1-position, with from 1 to 3 moles of a lower alkylene oxide.

* * * * *